United States Patent
Cotter et al.

(10) Patent No.: US 7,824,358 B2
(45) Date of Patent: Nov. 2, 2010

(54) HEART PUMP CONNECTOR

(75) Inventors: Christopher J. Cotter, Amesbury, MA (US); Olivier C. Bataille, Chazy, NY (US)

(73) Assignee: Thoratec Corporation, Pleasanton, CA (US)

( * ) Notice: Subject to any disclaimer, the term of this patent is extended or adjusted under 35 U.S.C. 154(b) by 540 days.

(21) Appl. No.: 10/897,311

(22) Filed: Jul. 22, 2004

(65) Prior Publication Data

US 2006/0074271 A1 Apr. 6, 2006

(51) Int. Cl.
*A61M 39/00* (2006.01)

(52) U.S. Cl. .......................... 604/6.16; 604/6.1; 604/7; 604/8; 604/9; 604/10; 623/3.26; 600/16

(58) Field of Classification Search ............... 604/6.1, 604/6.16, 7–10; 623/3.26; 128/912
See application file for complete search history.

(56) References Cited

U.S. PATENT DOCUMENTS

| | | | |
|---|---|---|---|
| 4,003,382 A | 1/1977 | Dyke | |
| 4,133,303 A | 1/1979 | Patel | |
| 4,564,014 A | 1/1986 | Fogarty et al. | |
| 4,619,640 A * | 10/1986 | Potolsky et al. | 604/7 |
| 4,955,856 A | 9/1990 | Phillips | |
| 5,242,418 A | 9/1993 | Weinstein | |
| 5,334,153 A | 8/1994 | McIntyre et al. | |
| 5,360,401 A | 11/1994 | Turnland | |
| 5,391,172 A | 2/1995 | Williams et al. | |
| 5,425,714 A | 6/1995 | Johnson et al. | |
| 5,445,646 A | 8/1995 | Euteneuer et al. | |
| 5,458,615 A | 10/1995 | Klemm et al. | |
| 5,571,135 A | 11/1996 | Fraser et al. | |
| 5,578,009 A | 11/1996 | Kraus et al. | |
| 5,591,138 A | 1/1997 | Vaillancourt | |
| 5,653,684 A | 8/1997 | Laptewicz et al. | |
| 5,674,192 A | 10/1997 | Sahatjian et al. | |
| 5,685,865 A | 11/1997 | Cosgrove et al. | |
| 5,695,469 A | 12/1997 | Segal | |
| 5,755,708 A | 5/1998 | Segal | |
| 5,861,010 A | 1/1999 | Boussignac et al. | |
| 5,882,334 A | 3/1999 | Sepetka et al. | |
| 5,911,728 A | 6/1999 | Sepetka et al. | |
| 6,001,056 A | 12/1999 | Jassawalla et al. | |
| 6,007,478 A | 12/1999 | Siess et al. | |
| 6,050,975 A | 4/2000 | Poirier | |
| 6,123,725 A | 9/2000 | Aboul-Hosn | |

(Continued)

OTHER PUBLICATIONS

HeartMate® XVE Inflow Valve—New Hardware Design Powerpoint Presentation given Jul. 31, 2003, 8 pages.

(Continued)

*Primary Examiner*—Carl H Layno
*Assistant Examiner*—Yun Haeng Lee
(74) *Attorney, Agent, or Firm*—Fish & Richardson P.C.

(57) ABSTRACT

A heart assist device connection system comprises an inflow connector in fluid-tight communication with an inflow section of a heart assist device. The connector is configured to be releasably connected to an inlet extension inserted into a patient's ventricle. The connector has one or more recesses configured to match a protrusion on the inlet extension. The system also comprises an outflow connector in fluid communication with an outflow section of the heart assist device. The outflow connector is configured to be releasably connected to a conduit attached-to the patient's vasculature.

18 Claims, 8 Drawing Sheets

U.S. PATENT DOCUMENTS

| | | | |
|---|---|---|---|
| 6,186,999 | B1 | 2/2001 | Chen |
| 6,217,548 | B1 | 4/2001 | Tsugita et al. |
| 6,802,806 | B2 | 10/2004 | McCarthy et al. |
| 2002/0095210 | A1* | 7/2002 | Finnegan et al. ........... 623/3.26 |
| 2002/0111577 | A1* | 8/2002 | Sirimanne et al. .......... 604/6.16 |
| 2003/0023255 | A1* | 1/2003 | Miles et al. ................. 606/158 |
| 2004/0059178 | A1 | 3/2004 | McCarthy et al. |

OTHER PUBLICATIONS

HeartMate® XVE Inflow Valve—New Hardware Design Powerpoint Presentation given Jun. 18, 2003, 7 pages.

Bernhard et al., "Perioperative Myocardial Infarction and Shock: Successful Management with a Left Ventricular Assist Device," *Myocardial Revascularization*, 1981, Mason and Collins (eds.), Yorke Medical Books, 4 pages.

Bernhard et al., "Paracorporeal left ventricular assist device," *Modern Technics in Surgery*, 1980, 14 pages.

Bernhard et al., "Clinical and Laboratory Investigations Related to Temporary and Permanent Ventricular Bypass," *Heart Transplantation*, 1983, 3(1):16-18.

Bernhard et al., "A new method for temporary left ventricular bypass," *J. Thor. Cardiovasc. Surg.*, 1975, 70(5):880-895.

Bernhard et al., "A Temporary Ventricular Assist Device for Patients Exhibiting Intractable Post-Cardiotomy Shock," *Assisted Circulation*, 1984, vol. 2, 10 pages.

Bourque et al., "HeartMate III: Pump Design for a Centrifugal LVAD with a Magnetically Levitated Rotor," *ASAIO Journal*, 2001, 47(4):401-405.

Buck et al., "A Volume Sensor For A Pneumatically Driven LVAD," *ASAIO Transactions*, 1979, 25:260-265.

Farrar et al., "Effectiveness of Design Improvements and Patient Management to Reduce Mechanical Malfunctions and Infections with the HeartMate® VE LVAS in the REMATCH Clinical Trial," Heart Failure and Circulatory Support Summit, Cleveland, Aug. 22-25, 2002, 1 page.

Gregoric et al., "A Newly Designed Inflow Valve Conduit for the Thoratec HeartMate XVE (In vivo Testing)," *ASAIO Journal*, 2003, 49(2):Poster Abstract.

Griffith et al., "HeartMate II Left Ventricular Assist System: From Concept to First Clinical Use," *Ann. Thorac. Surg.*, 2001, 71:S116-120.

Hegyeli and Machesko, "Report on Left Ventricular Assist Device," U.S. Department of Health, Education, and Welfare Publication, Jan. 1974, 3 pages.

Loree II et al., "The HeartMate III: Design and In Vivo Studies of a Maglev Centrifugal Left Ventricular Assist Device," *Artificial Organs*, 2001, 25(5):386-391.

Maher et al., "HeartMate Left Ventricular Assist Devices: A Multigeneration of Implanted Blood Pumps," Artificial Organ, 2001, 25(5):422-426.

Ozawa et al., "Inflow System for Long-term Left Ventricular Assist Device (LVAD)," *ASAIO Transactions*, 1980, 26:24-28.

\* cited by examiner

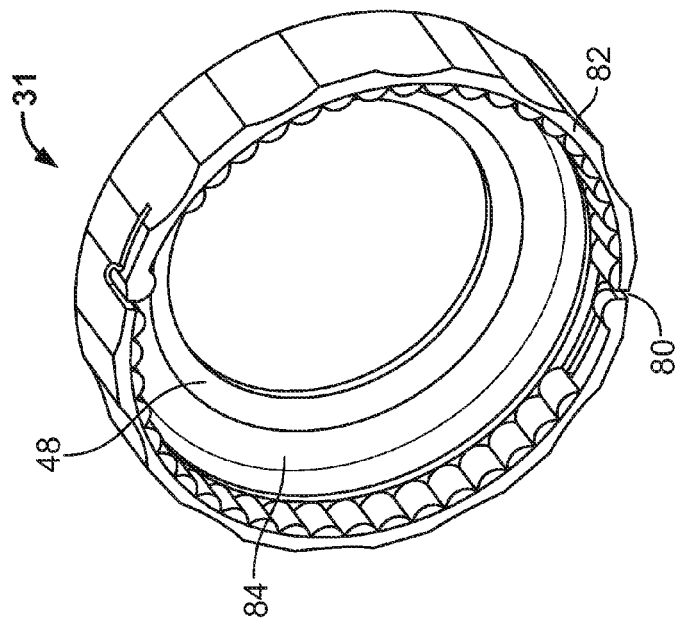
FIG. 6C
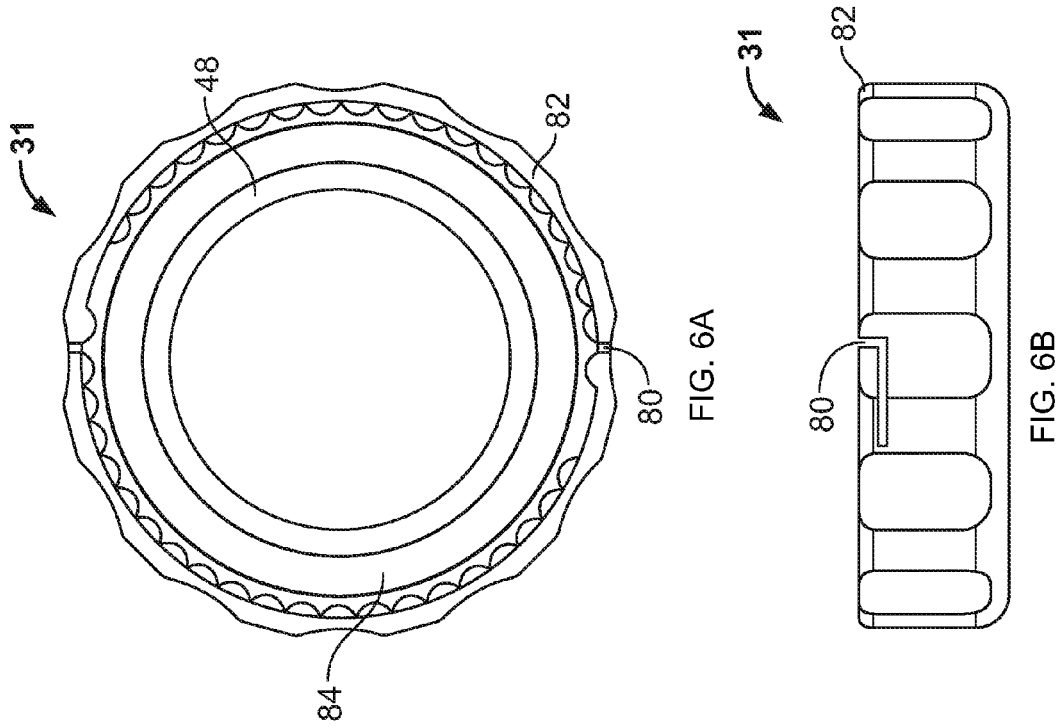
FIG. 6A
FIG. 6B

HEART PUMP CONNECTOR

TECHNICAL FIELD

This invention relates to apparatuses to assist the heart in pumping blood, and more particularly to heart assist device connectors.

BACKGROUND

Heart assist devices can take a number of forms. In one form, a pump is inserted in the circulatory system so as to draw blood from the ventricle and provide it to the vasculature. Such a pump is known as a ventricular assist device, or VAD. A VAD is useful when the ventricle is incapable of providing adequate blood flow alone.

While some VADs can provide a permanent solution for a weakened or dysfunctional ventricle, that is not always the case. For example, the VAD may simply be used as a bridge-to-transplantation implant, where the need for assistance is immediate, but a donor heart is not yet available. In such a case, when the heart is removed, the connection to the ventricle is removed. Also, it may be desirable to remove a VAD if the condition of the heart improves, in which case both connections could possibly remain, and would need to be covered, or plugged. In another case, it may be desirable to replace the implanted pump or a component, for example, if a different size pump is needed, if an improved pump is developed, or if the implanted pump or a component has operating troubles.

It is preferable to replace a pump in the most atraumatic manner possible, and typically without removing or destroying any connections to the patient's tissue. Replacing one pump or component with another, or covering conduits that serve a pump when the pump is removed, can be difficult. Specifically, open heart operations have both time and space constraints, as the chest cavity does not provide much room for a surgeon to work, and an operation provides less stress on the patient if it can be completed quickly with minimum tissue trauma. At the same time, the chest cavity can contain blood and other fluids during surgery, which can cover blood pump connectors so that they are hard to see, and so that they are slippery and hard to grasp. Thus, there is a need for connectors that can be manipulated well within the operational confines of surgery. At the same time, the connectors also need to provide a stable, strong, and reliable connection while working in a hostile environment, and connected to a moving object—the heart.

SUMMARY

The invention relates to connectors for use with an heart assist device. The connectors provide for reliable connection between a patient's heart or vasculature and the heart assist device, such as a left ventricular assist device or LVAD. The connectors also provide for relatively convenient connecting and disconnecting of heart assist devices.

In one embodiment, a heart assist device connection system is provided comprising an inflow connector in fluid-tight communication with an inflow section of a heart assist device and configured to be releasably connected to an inlet extension inserted into a patient's ventricle. A plurality of recesses, which may include a plurality of internal peripheral scallops, may be provided on the inflow connector to match a protrusion on an inlet extension. The system also comprises an outflow connector in fluid-tight communication with an outflow section of the heart assist device and configured to be releasably connected to a conduit attached to the patient's vasculature. A plurality of recesses, which may include a plurality of internal peripheral scallops, may be provided on the outflow connector to match a protrusion on an outflow graft. Also, the inflow and outflow connector may include a cylindrical backflow preventing valve mounted inside a reinforcing sleeve.

The inflow connector may define a first diameter, and the outflow connector may define a second diameter substantially different than the first diameter so as to prevent reversed connection of the system. The inflow or outflow connector may also have external peripheral threads to receive a screw ring so as to hold the assembly in fluid-tight connection. The external peripheral threads may have a major diameter of about 1.245 inches and about 32 threads per inch.

A reinforcing sleeve may also be held between the inflow connector and the inflow section of the heart assist device, and a valve may be mounted inside the reinforcing sleeve to prevent substantial fluid flow through the system in one direction. In addition, a reducing fitting may be located between the inlet extension and the inflow section of the heart assist device, and the reducing fitting may decrease in cross section from the inflow connector to the cannula. The inflow connector may also define an inner diameter in proximity to the inlet connections that is substantially the same as an inner diameter defined by the inlet extension, such as about 0.750 inches.

In another embodiment, a heart assist device connector is provided, comprising an inlet conduit that is in fluid communication with a heart assist device, an attachment ring having a ring surface configured to be attached to a corresponding surface on the inlet conduit, and a connector element having a first end and a second end, and configured to be received at the first end between the ring surface and the conduit surface, and further configured to be received at the second end by a connection fitting. A reinforcing sleeve may also be provided surrounding the connector element between the screw ring and the connection fitting. The connector element may comprise a generally cylindrical graft or a valve, such as a valve comprised of xenographic tissue or a back-flow preventing valve. The ring surface may also comprise a threaded portion, including female threads that mate with male threads on the conduit surface. A threaded plug may be provided and configured to be received inside the connection fitting, wherein the end of the connector element is secured between a threaded surface of the connection fitting and the threaded plug. Also, the connector may comprise a ring having female threads engaged with male threads on the threaded fitting, and having a lip configured to hold the connector tightly to a cannula.

In yet another embodiment a method of replacing a first heart assist device with a second heart assist device is disclosed. The first heart assist device has a pump body, an inflow section configured to attach to an apical conduit with a first threaded connector, and an outflow section configured to be attached to a conduit attached to a patient's aorta with a second threaded connector. The second heart assist device may have an inflow section configured to attach to the apical conduit, and an outflow section configured to attach to the conduit. The method may comprise disengaging the first threaded connector and the second threaded connector, removing the first heart assist device from the patient, positioning the second heart assist device in the patient to be connected to the apical connector and the conduit attached to the patient's aorta, and engaging the first threaded connector and the second threaded connector.

The method may also comprise providing a reducing conduit between the inflow section of the second heart assist device and the apical conduit. In addition, a reducing conduit may be provided between the outflow section of the second heart assist device and the conduit attached to the patient's aorta.

In another embodiment, a pair of universal connectors for connecting an inflow cannula to a heart assist device and for connecting the heart assist device to an outflow graft is provided.

A first connector has a first end with a threaded outer surface, a first outer diameter and a first inner diameter, a second end having a threaded surface, a second outer diameter and a second inner diameter, and a passage between the first end and the second end. The first connector is configured to mate with a tube at the first end and the heart assist device at the second end. A second connector comprises a first end having a threaded outer surface, a first outer diameter and a first inner diameter, a second end having a second outer diameter and a second inner diameter, and a channel passing between the first end and the second end. The first connector may be configured to mate with a graft at the first end and the heart assist device at the second end. The tube may comprise a screw ring surrounding at least a part of the tube, the screw ring having an inner threaded surface and being configured to mate with the threaded outer surface of the first end of the first connector.

In yet another embodiment, a method of replacing a first heart assist device with a second heart assist device is described, and comprises disconnecting an inlet conduit from the first device by rotating an inlet conduit screw ring, disconnecting an outlet conduit from the first device by rotating an outlet conduit screw ring, connecting the second device to the outlet conduit, aligning peripheral protrusion on the inlet conduit with scallops on the inlet insert, and connecting the second device to the inlet conduit.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 6A-6C show three views of a screw ring having a self-locking mechanism.

Like reference symbols in the various drawings indicate like elements.

DETAILED DESCRIPTION

Figure 1:
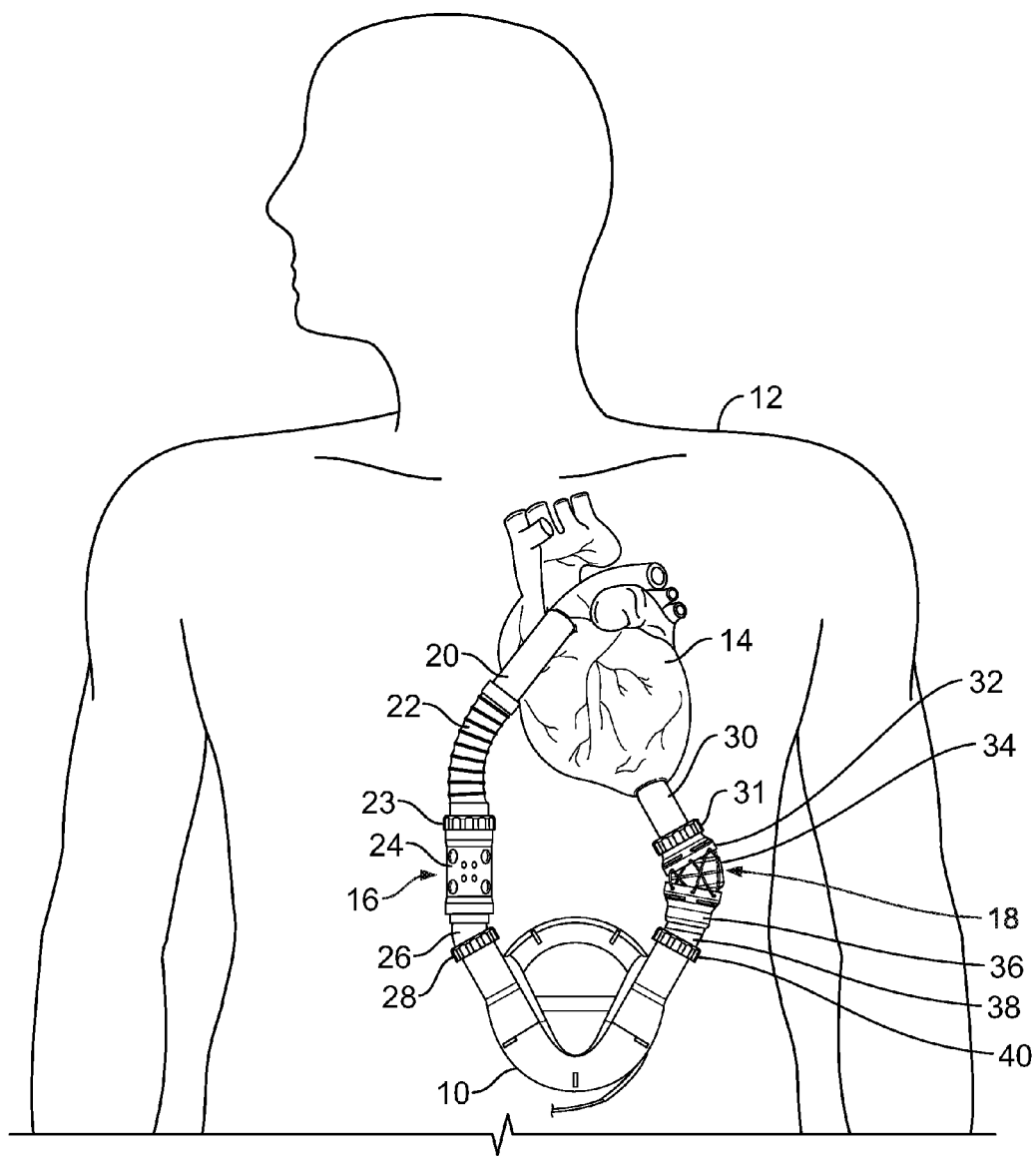
FIG. 1 shows a left ventricular assist device implanted in a human subject.

FIG. 1 shows a heart assist device 10 implanted in a human subject 12. The device 10 has an inflow section 18 and an outflow section 16, both extending from the body of device 10. The heart assist device 10 may be, for example, fully or partially implanted and pneumatically or electrically operated. The inflow section 18 receives the blood from the left ventricle and directs it into the device 10. In the device 10, the blood is forced through the outflow section 16 by, for example, a pusher plate, an axial rotor, or an impeller.

The inflow section extends from the apex of the subject's 12 left ventricle, while the outflow section includes a graft 20 anastomosed to the subject's 12 aorta. The graft 20 is sheathed by a flexible conduit 22 that may pass through the subject's 12 diaphragm and connects on its lower end to valve 24 with a screw ring 23 that slides over the flexible conduit 22. Valve 24 may be any manner of valve, such as a tissue or mechanical valve, that keeps fluid flowing forward through the device and prevents backflow from the aorta into the device. Alternatively, a non-pulsatile flow device that employs a rotor or impeller may only require an open conduit with no need for a valve at all.

Valve 24 is connected to an elbow 26 over which a screw ring 28 slides. The connection between valve 24 and elbow 26 may be a removable connection such as threads or a snap fit or may be a permanent connection such as a weld. The screw ring 28 allows the outflow section 16 to be connected to device 10.

The inflow side of device 10 starts with an apical cannula in the form of inlet extension 30, which is mounted in the left ventricle using, for example, sutures. The inlet extension 30 may also be surrounded by a cuff that holds the inlet extension 30 snugly and serves as an attachment point for the sutures. The inlet extension 30 may pass through the subject's 12 diaphragm and may have a screw ring 31 slid down its length to allow it to be connected solidly to inlet bell 32. For example, inlet bell 32 may have formed on its end closest to the heart male threads configured to mate with female threads on screw ring 31. A circumferential flange may be provided on the inlet extension 30 to prevent the screw ring 31 from sliding off the inlet extension 30. The inlet bell 32 is generally funnel-shaped and at its larger end surrounds a flexible connector 34. A similar outlet bell 36 is connected to the other end of flexible connector 34, so that inlet bell 32 may articulate relative to outlet bell 34 to permit flexibility in the location of inlet extension 30, whether during insertion of inlet extension 30 into the ventricle, or after installation when the heart and other parts of the subject 12 are moving. The outlet bell 36 is in turn connected to outlet elbow 38 which may have a flange at one end against which a screw ring 40 sits to hold inflow section 18 tight against the inlet of device 10. Each of the screw rings 23, 28, 31, 40 may be tightened to form a fluid-tight seal so as to prevent fluids from leaking out of the system during operation. They may also be provided with appropriate locking features that prevent them from loosening after the device 10 has been implanted. Also, although the connectors are described as using screw rings, they make take any other appropriate form that allows for reliable connections. Examples of such connectors may include twist-and-lock connectors, connectors with bolted flanges, circumferential clamps, compressive fitting, snap fit, or simple threaded connections.

The various connectors may be sized to allow interchangeability of pumps without the need to remove graft 20 or inlet extension 30 from the aorta or heart. To accomplish the interchangeability, various components, such as eblow 26, 38 may have non-constant diameters, so as to be larger on one end than on the other. Also, inlet bell 34 and outlet bell 36 may have different end connection sizes, or valve 24 may be different sizes at its two ends. The various component parts may also take other appropriate forms, and may be different in number than those pictured. Parts, fittings, and connectors may also be flexible or rigid as required. Also, where fittings take the form of male/female, the order of the fittings may be reversed, as appropriate.

The various parts of the system may be constructed from any appropriate and adequately durable materials. For example, flexible connectors, such as flexible conduit 22 and flexible connector 34 may be made from PTFE, polyester, polyurethane, silicone, or other biocompatible material. The other structural components, such as inlet extension 30, inlet bell 32 and outlet bell 36, the housing for valve 24, elbows 26, 38, and screw rings 23, 28, 31, 40, may be made from titanium or titanium alloy, stainless steel, or a plastic of appropriate strength that is capable of sterilization and long term implantability. Where possible, the surfaces of the various parts, and in particular, the interior blood contacting surfaces, may be roughened or coated so as to provide for the formation of a pseudo neo-intima upon implantation to reduce the incidence of thromboembolism.

In use, the device 10 can be exchanged with a different device by removing screw ring 32 from the inflow section 18 and screw ring 23 from the outflow section 16. Screw ring 28 or screw ring 40 could also or alternatively be removed. The surgeon may then remove the device 10, and place a new device in its place. The surgeon may then align the new device with inflow section 18 and outflow section 16 and tighten the corresponding screw ring. This procedure can be simplified, or modified to replace individual device components, using features of the connectors described in more detail below. Also, the process is simplified where the replacement inflow and outflow connectors have the same diameter as the original inflow and outflow connectors. Where the diameters of the old and new devices differ, reducing connectors may be used. Also, as necessary for functional reasons, or to prevent an original or replacement device from being installed backward, one or more of the inlet components may be produced to a different shape or size than the outlet components, or may be provided with a feature or features (such as a mating spline) that prevents connection of outlet components to inlet components.

Figure 2:
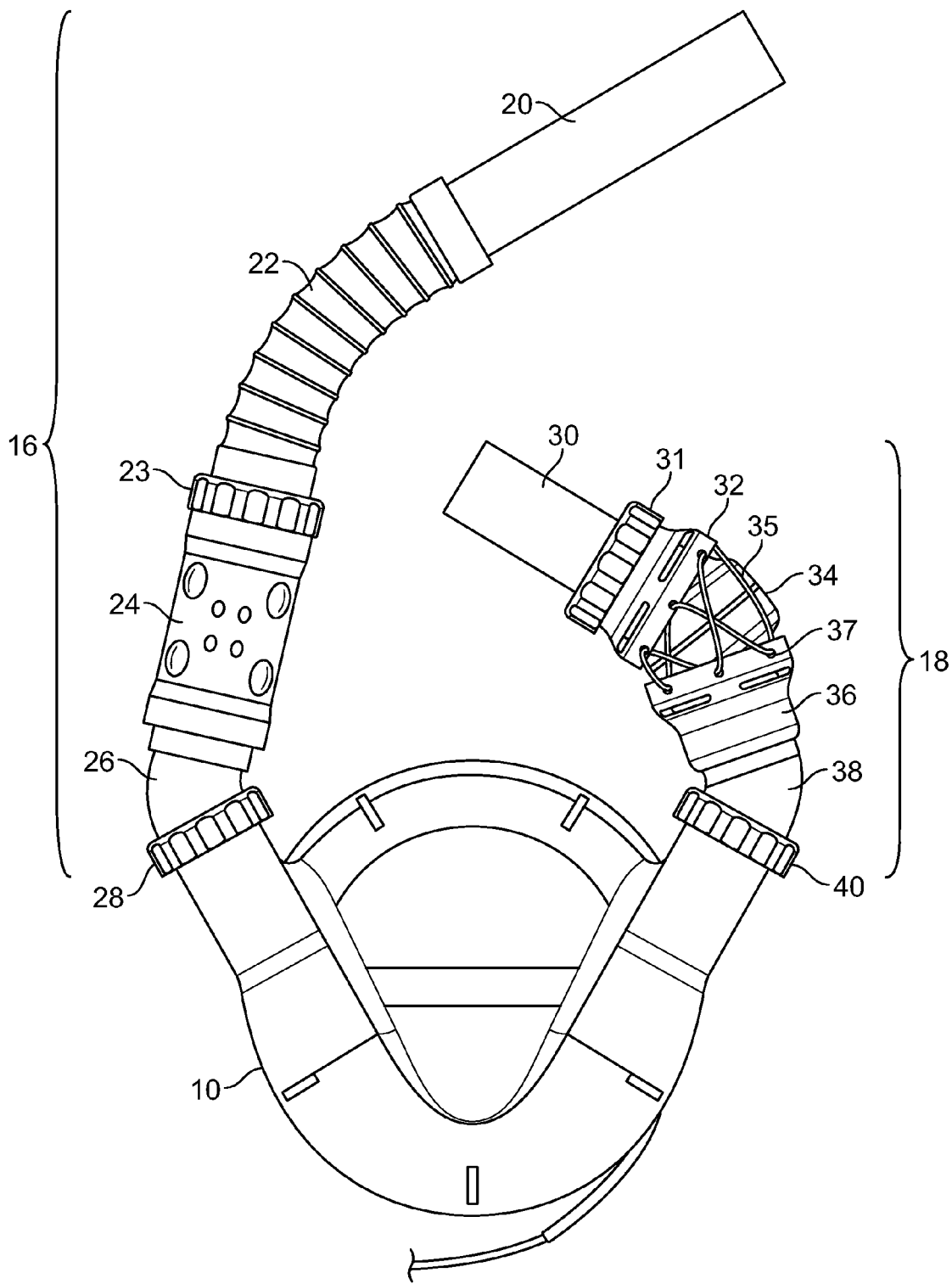
FIG. 2 shows the left ventricular assist device in greater detail.

FIG. 2 shows the left ventricular assist device 10 in greater detail. Again, the device is shown with an inflow section 18 connected to one side, and an outflow section 16 connected to the other. Both sections 16, 18 connect to the device 10 with elbows 26, 38 secured by threaded screw rings 28, 40. As with the other components of the system, the elbows 26, 38 can have varying degrees of curvature or linearity, depending on the size of device 10, and the location at which the inflow section 18 enters the ventricle, and the outflow section 16 enters the aorta. The elbows 26, 38 may also be rigid or flexible, and may have varying cross-sections. The flexible conduit 22 surrounding graft 20 is shown as having multiple segments, which may be areas in which the conduit is compressed and folded back on itself, to permit for articulation of the flexible conduit 22, similar to the construction of a flexible drinking straw, but providing an inner surface that is more rounded than that of a drinking straw. The flexible conduit 22 may be flared at one end and received inside screw ring 23, or may be bonded or compressed onto a separate rigid fitting that in turn has a lip that can be held by screw ring 23.

The inflow section 18 is shown to have symmetrical bells 32, 36 that cup the flexible connector 34. The bells 32, 36 are held in place, but allowed to flex, by the tension in cords 35, which may be one or more 0.03 inch diameter PTFE monofilaments or other appropriate material. Pins 37 may be provided between a pair of rings that form the periphery of bells 32, 36, and cords 35 may be laced over them. In this manner, cords 35 may stretch on one side and contract on the other side of flexible connector 34 when the inflow section bends. The cords 35 may slide over the pins 37 to redistribute the cords 35 to the side on which it is needed.

Figure 3:
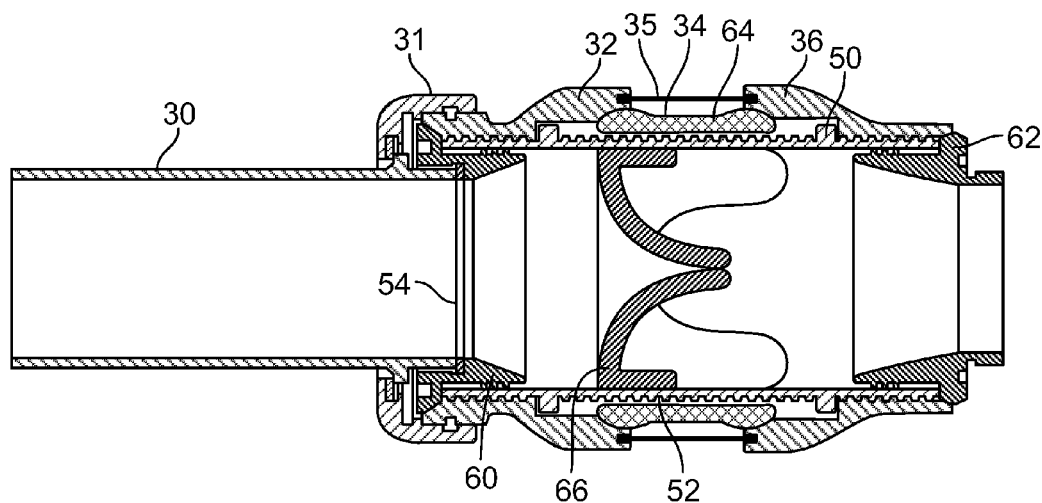
FIG. 3 is a cross section of an inflow valve assembly for a left ventricular assist device.

FIG. 3 is a cross section of an inflow valve assembly for a left ventricular assist device. The assembly is positioned so that its left end would connect to a subject's ventricle, and its right side would be near a cardiac assist device. The assembly comprises a pair of bells 32, 36 with their enlarged openings facing each other. A flexible connector 34 is mounted between the bells 32, 36, and may be, for example, a PTFE sleeve 64 wrapped around the periphery of a rigid titanium alloy cylinder 52 surrounding the valve assembly. The flexible connector may be held in place, where the assembly is straight, by the edges of the bells 32, 36.

A graft 50 runs inside the flexible connector 34, and may be considered to be a part of the valve's flexible connector. The graft 50 may serve to provide a flexible pathway for fluid flow through the assembly, and may be constructed in any appropriate form and from any appropriate material or materials to enable such fluid flow. At both ends of the flexible connector, the graft 50 is secured between protrusions formed on the inner periphery of bells 32 and 36, and protrusions formed on the outer periphery of inserts 60 and 62. The protrusions on bells 32 and 36 may be spiral threads configured to mate with threads on inserts 60 and 62. The graft 50, possibly having a number of stacked ribs about its external periphery, may be seated within the female threads of the bells 32 and 36, then secured between the bells and inserts by carefully advancing the male threads of the inserts into the bells.

Inlet insert 60 tapers outward as it moves away from the subject's heart, so as to provide smooth transitional flow through the insert 60 to graft 50 and valve 66 with minimal flow disturbance. Inlet extension 30 may have a circular end face configured to mate flush against inlet insert 60, and may be held in place by screw ring 31 pushing against a circumferential flange on the inlet extension 30. A washer 54, such as a PTFE washer or other appropriate material to maintain a long-lasting seal, may also be provided between the inlet extension 30 and the inlet insert 60.

Inlet insert 60, or any other portion of the assembly near the inner opening of inlet 30 extension 30 may be sized to permit smooth fluid flow from inlet extension 30 and through the assembly. For example, the relevant component may have a round inner diameter at its one edge that matches the inner diameter of inlet extension 30, or is about the same diameter so as to prevent disruptions in fluid flow that would affect the short-term or long-term operation of the system. As one example, the inner diameter of the inlet extension 30 and the inlet insert 60 or other component in proximity to the inlet insert 30, may be approximately 0.750 inches. Alternatively, the inner diameter may be about 0.512 inches. Also, the outer surface of bell 32 may be configured and sized to mate properly with an inner surface of screw ring 31. For example, bell 32 may be provided with male threads having a major diameter of about 1.245 inches and about 32 threads per inch.

The valve element 66 allows blood flow only away from the heart, and thus serves to ensure unidirectional flow, where such constriction is necessary. The valve element 66 may be made of bovine, porcine, equine or ovine tissue or a synthetic biocompatible material and may take a generally toroidal form, possibly having one or more moveable sections that may be triangular and convex in shape with the inner portion, falling to a point when the valve is closed, and increasing to a circle when the valve is opened or opening. The valve element 66 also has shoulders about its outer periphery that run along the inner surface of graft 50 and may be held in place by stitching between valve element 66 and graft 50, or in any other appropriate manner. Alternatively, a non-pulsatile flow device that employs a rotor or impeller may only require an open conduit with no need for a valve at all.

As with the inflow assembly 18 (see FIG. 2), the outflow assembly 16 may have components appropriately sized to allow for an easy exchange of pumps while maintaining any components that interface with the patient in place. For example, flexible conduit 22 may have an inner diameter at the end closest to the pump (or in a connector at that end) matched to the inner diameter of valve 24 or any assembly in the place of valve 24. Likewise, the inner diameter of the outlet of device 10 may substantially match that of elbow 26. For example, the relevant component may have a round inner diameter at one edge that matches the inner diameter of the mating component, or is about the same diameter so as to prevent disruptions in fluid flow that would affect the short-term or long-term operation of the system. As one example, the inner diameter of the device end of the flexible conduit 22 and the valve 24, may be approximately 0.750 inches. Alternatively, the inner diameter may be about 0.512 inches. Also, the outer surface of valve 24 or other relevant component or the outlet of device 10 may be configured and sized to mate properly with an inner surface of screw rings 23, 28, as is appropriate. For example, valve 24 may be provided with male threads having a major diameter of about 1.050 inches and about 32 threads per inch, or device 10 outlet may be provided with male threads having a major diameter of about 0.840 inches and about 32 threads per inch. Also, relevant components on the outlet side may be purposefully configured so as to be different from those on the inlet side, so as to minimize the chance for errors in implanting the device 10.

Figure 4:
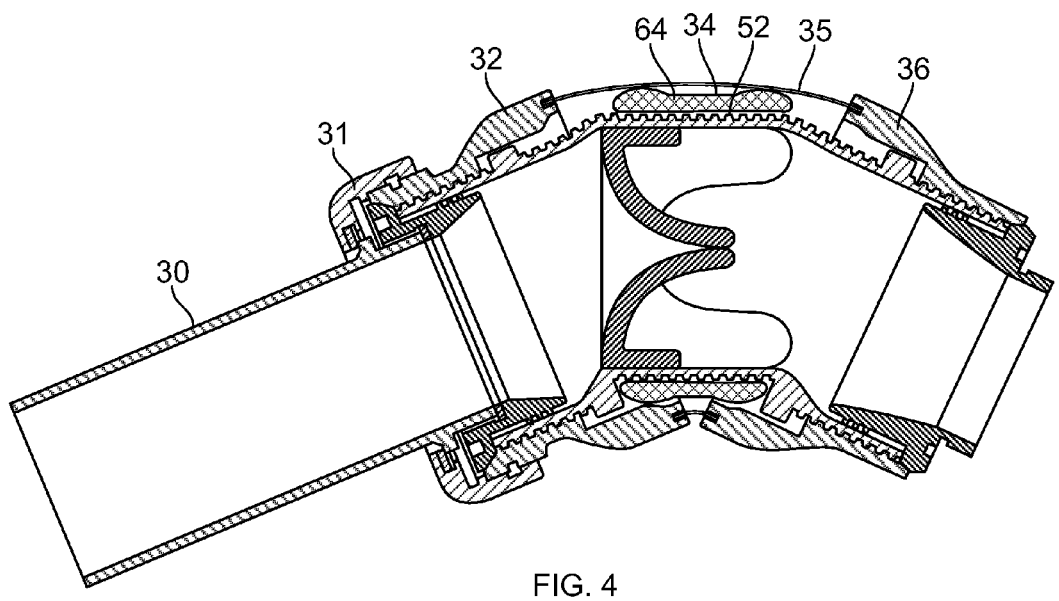
FIG. 4 is the inflow valve assembly of FIG. 3 flexed to one side.

FIG. 4 shows the inflow valve assembly of FIG. 3 flexed to one side. The assembly is shown articulated to forty-seven degrees from its unflexed state. As can be seen in the figure, flexible connector 34 generally maintains its cylindrical shape, and becomes held tightly in place on the lower side of the valve assembly by the shoulders of inlet bell 32 and outlet bell 36. The flexible connector 34 is held in place on the other side by cords 35, which have become stretched tightly over flexible connector 34. There is no slack shown in cords 35 on the lower side of the assembly, because the slack has been picked up by the extension of cords 35 on the top of the assembly. Also, the PTFE sleeve 64 and cylinder 52 of flexible connector 34 maintains a constant cross-sectional area for valve element 62 so that valve element 62 is not pushed out of its natural shape. Also, graft 50 stretches and flexes to provide a single relatively smooth surface to avoid interference with blood flowing through the assembly.

Figure 5:
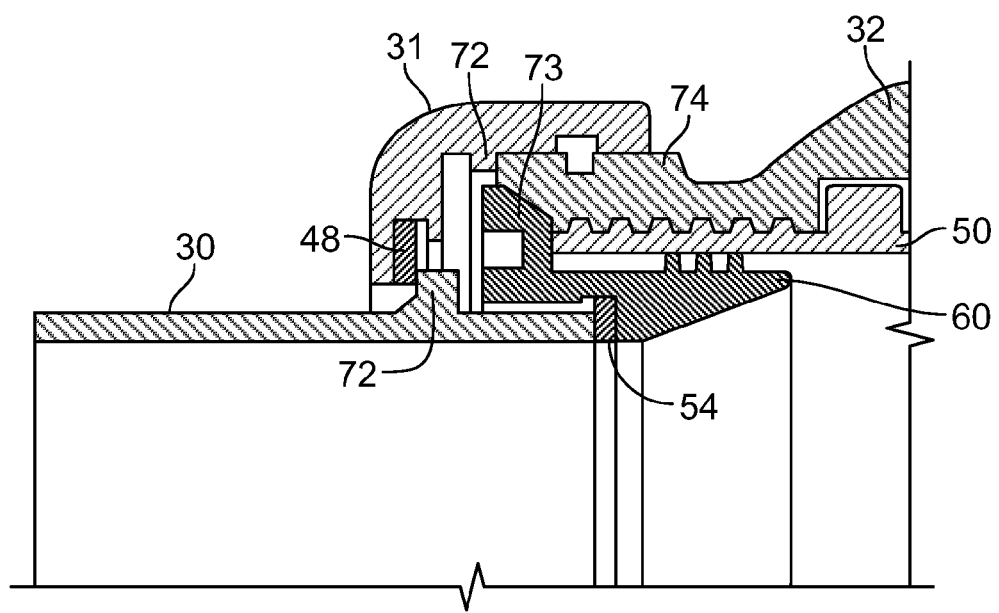
FIG. 5 is a detailed cross section of a portion of the inflow valve assembly of FIG. 3.

FIG. 5 is a detailed cross section of a portion of the inflow valve assembly of FIG. 3. In general, the components are configured in a stack that is held tightly in place by screw ring 31, which has internal threads that screw onto external threads on bell 32. The shoulder of the screw ring 31 presses tight against a flange 72 on inlet extension 30, so that inlet extension 30 is held in place. A washer 48, such as a PTFE washer, may be held tight between screw ring 31 and flange 72 to facilitate tightening by reducing the friction between the shoulder of screw ring 31 and flange 72. The washer may also be made of another material or materials appropriate to the particular application.

The base of the inlet extension 30 presses tightly against a face seal washer 54 resting in an undercut of inlet insert 60. The washer 54 provides a solid, liquid-tight seal for the valve assembly. As described before, inlet insert 60 is threaded into bell 32 and is located and fixed by the friction between the circumferential beveled flange 73 and a complementary beveled surface on bell 32. The mating of the beveled surfaces of the inlet insert 60 and inlet bell 32 prevents fluid from passing out of the assembly along the outer periphery of insert 60. The bottom descending edge of screw ring 31 may also have a portion that extends slightly inward to rest against detent 74, as will be described in more detail with regard to FIG. 6.

FIGS. 6A-6C show three views of a screw ring 31 having a self-locking mechanism 80. The screw ring 31 generally has a flat ring portion 84 with a descending wall 82 around the outer circumference of the flat ring portion 84. Washer 48 is secured in an undercut located circumfrentially around the peripheral edge of the flat ring portion 84, to reduce friction at the interface with inlet extension 30 (FIG. 5).

Self-locking mechanism 80 provides a structure by which screw ring 31 may be prevented from loosening once it is tightened on a connector. As shown, self-locking mechanism 80 is a thin cantilevered arm cut from a portion of descending wall 82. The terminal portion of the arm is rounded slightly toward the center of the screw ring 31 to create a smoothed edge that can contact an outer edge of detents 74 on bell 32 (see FIG. 5). In this manner, a simple yet effective mechanism is provided to prevent unwanted rotation of the screw ring 31. In addition, the contact between self-locking mechanism 80 and the various detents 74 provides a physician with tactile feedback concerning the rotational progress of the screw ring 31. In addition, the resistance between the self-locking mechanism 80 and the detents 74 remains generally constant, so that the physician can better determine when the screw ring 31 has been fully tightened.

Figures 7A, 7B:
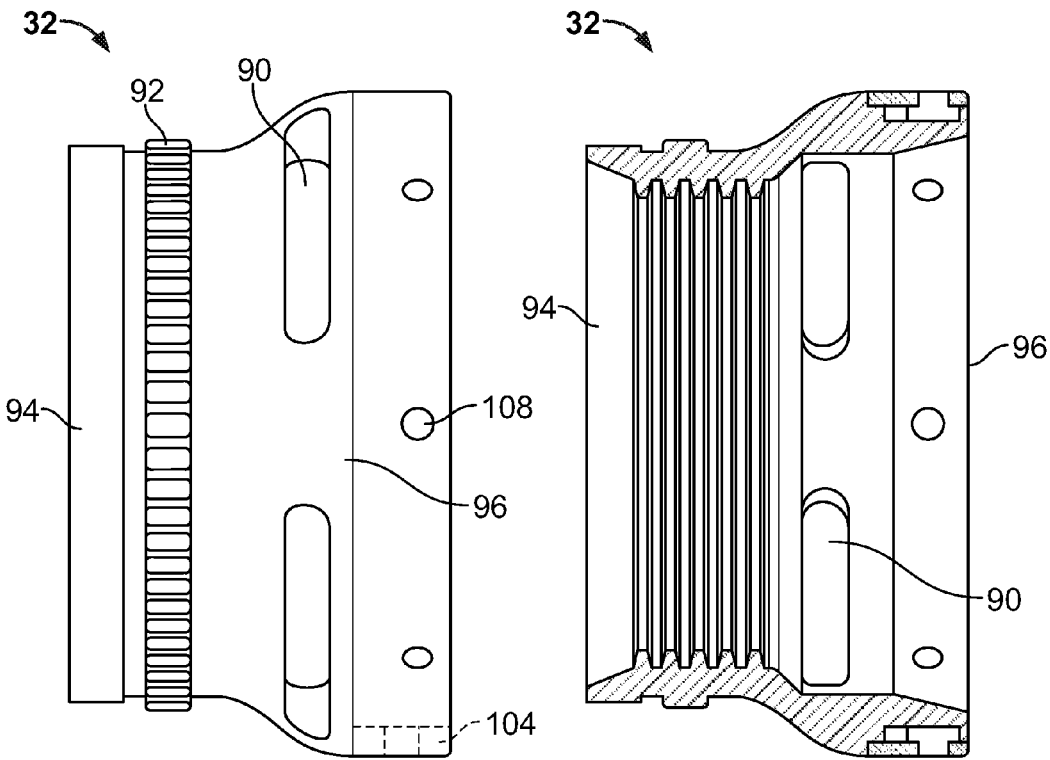
FIGS. 7A-7C show three views of an inlet bell for use in an inflow valve assembly.
Figure 7C:
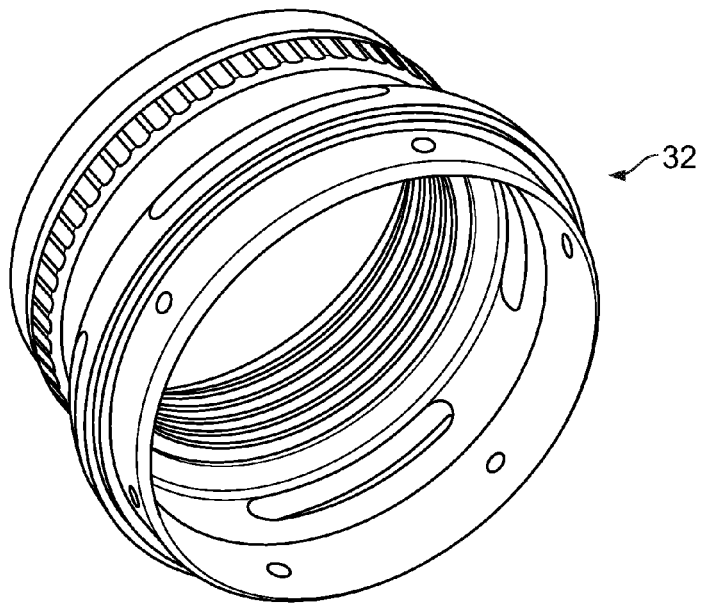

FIGS. 7A-7C show three views of an inlet bell 32 for use in an inflow valve assembly. In general, the inlet bell 32 serves as a connection point for the various components of an inflow section. The inlet bell 32 has a tapered opening 96 at one end, and a narrower cylindrical end 94 of constant cross-section at the other. The tapered end 96 may have a number of passages 90 formed in its outer periphery to allow visual and physical access to graft 50 and facilitate pre-clotting or sealing of graft 50 at the time of implant. The tapered end 96 may also be necked-in slightly to accept a band 104 about its periphery, which may be welded to 96, and may hold together a plurality of pins 108 spaced around the periphery of the band 104. The pins may then serve as anchoring points for the cords that hold the bells in flexible tension.

In a middle portion of inlet bell 32, a ring 92 of detents 74 is provided as a generally undulating pattern about the periphery. As described above, the detents 74 are configured to come into contact with an extension from a screw ring so as to prevent unwanted rotation of the screw ring.

Figure 8A:
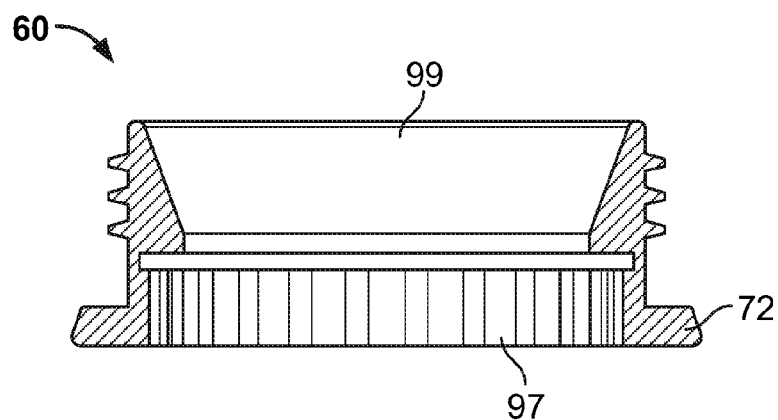
FIGS. 8A and 8B show a cross-section and top view of an inlet insert.
Figure 8B:
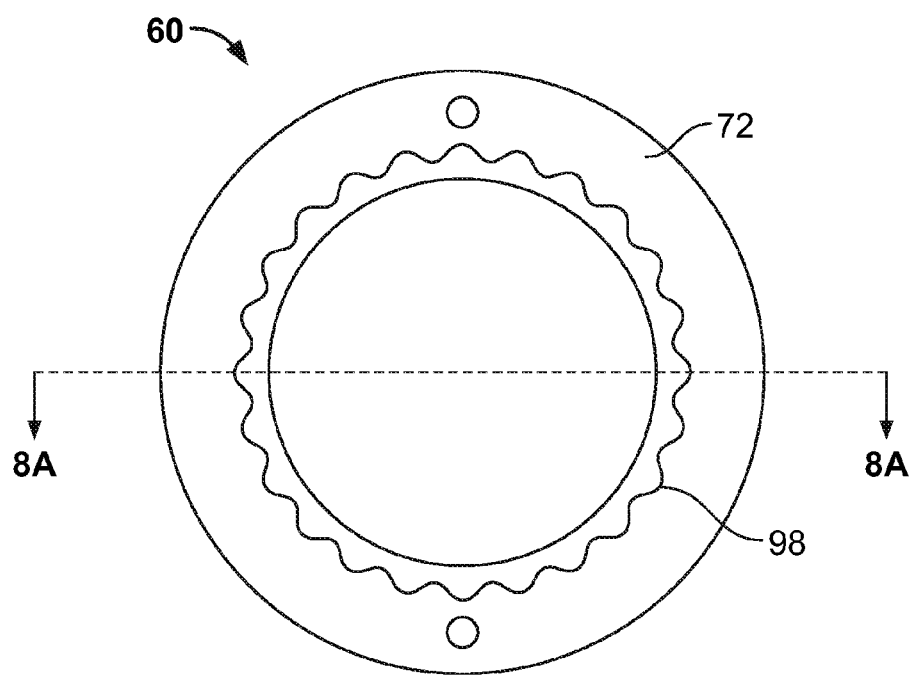

FIGS. 8A and 8B show a cross-section and top view of an inlet insert 60. The insert 60 has a tapered opening 99 at one end, and an untapered opening 97 at the other end. The tapered end 99 provides for smooth transfer of fluid flow through insert 60 to graft 50. The untapered end 97 is provided with a plurality of scallops 98 around its inner periphery. The scallops provide a number of locations to receive a protrusion 112 on the outer periphery of the neck 110 of inlet extension 30 shown in FIG. 9. Flange 114 on inlet extension 30 provides a surface for screw ring 31 to apply a force to seat the face of inlet extension 30 against the face of inlet insert 60.

The use of a protrusion 112 in relation to scallops 98 provides a number of advantages for the use of a connector. For example, the mating at an interior portion of insert 60 provides for a more isolated face seal between the inlet extension 30 and the insert 60. Also, the inlet extension 30 can be implemented with a single protrusion to provide a variety of possible angular fixations within the plurality of scallops, facilitating the placement of a new component or pump. Another number of protrusions may also be selected as desired. Moreover, the face seal can be held flat and tight once the screw ring is placed on the connector. The joint thus allows for axial alignment between the inlet extension 30 and a pump, and prevents unwanted rotational motion after a new pump has been installed. The joint is relatively simple and can be aligned easily, and made or broken via the screw ring 31 even in a bloody field.

Figure 9:
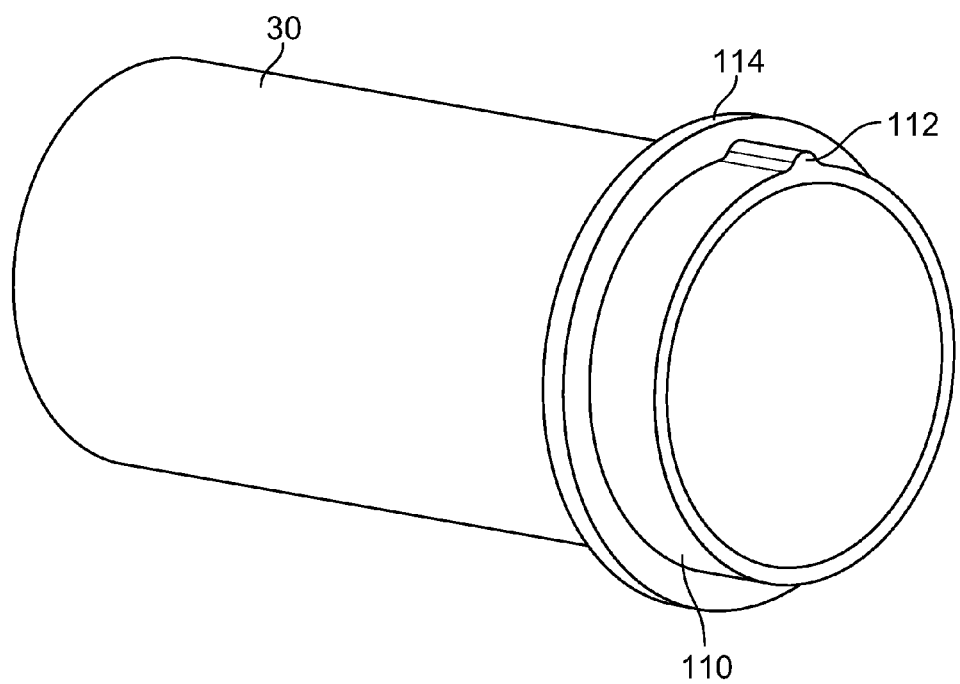
FIG. 9 shows an inlet extension that may connect a patient's vasculature to the components of a heart assist device.

FIG. 9 shows an inlet extension 30 that may connect a patient's vasculature to the components of a heart assist device. Inlet extension 30 contains a mating extension 110, which may be sized and configured as described above to interrelate with other components of a system for connecting a heart assist device. Shoulder 114 may extend outward from a portion or all of the periphery of inlet extension 30 to allow for the application of axial force that helps keep a seal where inlet extension 30 connects to other components. Protrusion 112 may mate with a corresponding form on a mating component, and may assist in aligning the inlet extension 30, and may also provent unwanted rotation of inlet extension 30 relative to the mating component, both during and after assembly.

A number of embodiments of the invention have been described. Nevertheless, it will be understood that various modifications may be made without departing from the spirit and scope of the invention. For example, the seal at the interface of inlet extension 30 and inlet insert 60 could be achieved via an o-ring or the anti-rotation feature could be a pin or snap-fit instead of a single protrusion. Accordingly, other embodiments are within the scope of the following claims.

What is claimed is:

1. A heart assist device connection system, comprising:
   an inflow connector in fluid-tight communication with an inflow section of a heart assist device and configured to be releasably connected to an inlet extension inserted into a patient's ventricle, the inflow connector defining a longitudinal axis parallel with a flow path through the inflow connector and having a plurality of recesses defining axes substantially parallel to the inflow connector longitudinal axis and configured to receive and match a protrusion on the inlet extension when the inlet extension is inserted in the inflow connector and to prevent rotation of the inlet extension relative to the inflow connector; and
   an outflow connector in fluid-tight communication with an outflow section of the heart assist device and configured to be releasably connected to a conduit attached to the patient's vasculature,
   wherein the inflow connector includes a stopping surface to engage the inlet extension so as to block insertion of the inlet extension into the inflow connector and to define a maximum depth of insertion of the inlet extension into the inflow connector, and wherein the recesses are defined to prevent rotation of the inlet extension relative to the inflow connector from initial insertion of the inlet extension into the inflow connector to the maximum depth of insertion.

2. The system of claim 1, further comprising a plurality of recesses on the outflow connector to match a longitudinal protrusion on an outflow graft.

3. The system of claim 1, wherein the inflow or outflow connector includes a cylindrical backflow preventing valve mounted inside a reinforcing sleeve.

4. The system of claim 1, wherein the one or more recesses includes a plurality of internal peripheral scallops.

5. The heart assist device connection system of claim 4, where the internal peripheral scallops are define by a continuous undulating surface.

6. The system of claim 1, wherein the inflow connector defines a first diameter, and the outflow connector defines a second diameter substantially different than the first diameter so as to prevent reversed connection of the system.

7. The system of claim 1, wherein the inflow or outflow connector has external peripheral threads to receive a screw ring that is mounted on the inlet extension and is rotatable independently of the inlet extension so as to hold the inlet extension in fluid-tight connection.

8. The system of claim 7, wherein the external peripheral threads have a major diameter of about 1.245 inches and about 32 threads per inch.

9. The system of claim 1, further comprising a reinforcing sleeve held between the inflow connector and the inflow section of the heart assist device.

10. The system of claim 9, further comprising a valve mounted inside the reinforcing sleeve to prevent substantial fluid flow through the system in one direction.

11. The system of claim 1, further comprising a reducing fitting between the inlet extension and the inflow section of the heart assist device.

12. The system of claim 11, wherein the reducing fitting decreases in cross section from the inflow connector to the inlet extension.

13. The system of claim 1, wherein the inflow connector defines an inner diameter in proximity to the inlet extension that is substantially the same as an inner diameter defined by the inlet extension.

14. The system of claim 13, wherein the inflow connector inner diameter is about 0.750 inches.

15. The heart assist device connection system of claim 1, wherein the plurality of recesses each define a pair of continuous faces that are directed toward each other and are substantially parallel to the inflow connector longitudinal axis from an end of the inflow connector that engages the inlet extension to the maximum depth of insertion of the inlet extension.

16. A pair of universal connectors for connecting an inflow cannula to a heart assist device and for connecting the heart assist device to an outflow graft, comprising:
   a first connector having at least one threaded outer surface, the first connector defining a passage of tapered varying diameter and configured to mate with a tube at a first end and the heart assist device at a second end that is opposed to the first end; and
   a second connector having at least one threaded outer surface, defining a through channel, and being configured to mate with a graft at a first end of the second connector and to the heart assist device at a second end of the second connector,
   wherein the threaded outer surfaces of the first connector and the second connector are located at ends of the first and second connectors so as to engage threaded rings on the tube and the outflow graft, respectively.

17. The universal connectors of claim 16, wherein the tube comprises a screw ring surrounding at least a part of the tube, the screw ring having an inner threaded surface and being configured to mate with the threaded outer surface of the first connector.

18. The connectors of claim 16, wherein each of the first and second connectors further comprise threaded surfaces, separate from the threaded outer surfaces of the first and second connectors, arranged to engage corresponding threaded surfaces of the heart assist device.

* * * * *